US00PP23138P2

(12) United States Plant Patent
Beekenkamp

(10) Patent No.: US PP23,138 P2
(45) Date of Patent: Oct. 23, 2012

(54) ***BEGONIA* PLANT NAMED 'BKBEWPF'**

(50) Latin Name: *Begonia pendula*
Varietal Denomination: BKBEWPF

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 27 days.

(21) Appl. No.: 12/932,731

(22) Filed: Mar. 4, 2011

(51) Int. Cl.
*A01H 5/00* (2006.01)

(52) U.S. Cl. ..... Plt./343

(58) Field of Classification Search ..... Plt./343
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'BKBEWPF', characterized by its semi-pendulous, spreading and mounded plant habit; freely basal branching habit; medium-size leaves; freely and continuously flowering habit; long flowering period; and single and semi-double flowers that are white to pink in color.

2 Drawing Sheets

Botanical designation: *Begonia pendula.*
Cultivar denomination: 'BKBEWPF'.

BACKGROUND OF THE INVENTION

The present invention relates to a new and distinct cultivar of *Begonia* plant, botanically known as *Begonia pendula*, and hereinafter referred to by the name 'BKBEWPF'.

The new *Begonia* plant is a product of a planned breeding program conducted by the Inventor in Amstelveen, The Netherlands. The objective of the breeding program was to develop new hanging *Begonia* plants with good outdoor performance and long flowering period.

The new *Begonia* plant originated from a cross-pollination made by the Inventor in March, 2007 of a proprietary selection of *Begonia pendula* identified as code number 07-002-04, not patented, as the female, or seed, parent with a proprietary selection of *Begonia pendula* identified as code number 06-276-08, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in April, 2008.

Asexual reproduction of the new *Begonia* plant by tip cuttings in a controlled greenhouse environment in Amstelveen, The Netherlands since May, 2009 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'BKBEWPF'. These characteristics in combination distinguish 'BKBEWPF' as a new and distinct *Begonia* plant:

1. Semi-pendulous, spreading and mounded plant habit.
2. Freely basal branching habit.

3. Medium-size leaves.
4. Freely and continuously flowering habit.
5. Long flowering period; plants flower throughout the summer in The Netherlands.
6. Single and semi-double flowers that are white to pink in color.

Plants of the new *Begonia* can be compared to plants of the female parent selection. Plants of the new *Begonia* differ from plants of the female parent selection in the following characteristics:

1. Plants of the new *Begonia* have darker green-colored leaves than plants of the female parent selection.
2. Plants of the new *Begonia* and the female parent selection differ in flower color as plants of the female parent selection have pale orange-colored flowers.

Plants of the new *Begonia* can be compared to plants of the male parent selection. Plants of the new *Begonia* differ primarily from plants of the male parent selection in flower color as plants of the male parent selection have white-colored flowers.

Plants of the new *Begonia* can be compared to plants of the *Begonia* 'Encanto Orange', disclosed in U.S. Plant Pat. No. 20,898. In side-by-side comparisons conducted in Amstelveen, The Netherlands, plants of the new *Begonia* differed from plants of 'Encanto Orange' in the following characteristics:

1. Plants of the new *Begonia* were not as pendulous as plants of 'Encanto Orange'.
2. Plants of the new *Begonia* had larger and darker green-colored leaves than plants of 'Encanto Orange'.
3. Plants of the new *Begonia* and 'Encanto Orange' differed in flower color as plants of 'Encanto Orange' had bright orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKBEWPF' grown in a container.

The photograph on the second sheet is a close up view of a typical flowering plant of 'BKBEWPF'.

DETAILED BOTANICAL DESCRIPTIONS

Plants used for the aforementioned photographs and following observations and measurements were grown in 27-cm containers during the winter in a glass-covered greenhouse in Maasdijk, The Netherlands. During the production of the plants, day temperatures averaged 19° C., night temperatures ranged from 17° C. to 18° C. and the daylength was extended to about 14 hours. Plants were pinched one time and were 20 weeks old when the photographs and the description were taken. In the following description, color references are made to The Royal Horticultural Society Colour Chart, 2007 Edition, except where general terms of ordinary dictionary significance are used.

Botanical classification: *Begonia pendula* 'BKBEWPF'.

Parentage:

*Female, or seed, parent*.—Proprietary selection of *Begonia pendula* identified as code number 07-002-04, not patented.

*Male, or pollen, parent*.—Proprietary selection of *Begonia pendula* identified as code number 06-276-08, not patented.

Propagation:

*Type*.—By tip cuttings.

*Time to initiate roots, summer*.—About one week at temperatures of about 20° C. to 25° C.

*Time to initiate roots, winter*.—About one week at temperatures of about 18° C. to 20° C.

*Time to produce a rooted young plant, summer*.—About 32 days at temperatures of about 20° C. to 25° C.

*Time to produce a rooted young plant, winter*.—About 35 days at temperatures of about 18° C. to 20° C.

*Root description*.—Medium in thickness, fibrous; white in color; plants of the new *Begonia* have not been observed to form tubers.

*Rooting habit*.—Moderate branching; medium density.

Plant description:

*Plant form and growth habit*.—Semi-pendulous, spreading and mounded plant habit; flattened globular in shape; freely basal branching with about five primary branches per plant; primary branches with secondary branches at potentially every node; moderately vigorous growth habit.

*Plant height*.—About 26.5 cm.

*Plant width*.—About 43.3 cm.

*Branch description*.—Length: About 17.5 cm. Diameter: About 7 mm. Internode length: About 3.2 cm. Texture: Slightly pubescent. Color: Close to 197A to 197B tinged with close to 152A to 152B.

*Leaf description*.—Arrangement: Alternate, simple. Length: About 12.3 cm. Width: About 5.7 cm. Shape: Ovate. Apex: Acuminate. Base: Oblique. Margin: Biserrate. Texture, upper and lower surfaces: Sparsely pubescent. Venation pattern: Palmate; reticulate. Color: Developing leaves, upper surface: Close to 200A to 200B tinged with close to 147A. Developing leaves, lower surface: Close to 187A to 187B. Fully expanded leaves, upper surface: Darker than 147A and N189A; venation, close to 147B. Fully expanded leaves, lower surface: Close to 148C; venation, close to 148A. Petioles: Length: About 3.8 cm. Diameter: About 4 mm. Texture, upper and lower surfaces: Sparsely pubescent. Color, upper surface: Close to 199A to 199B slightly tinged with close to 176B to 176C. Color, lower surface: Close to 199A to 199B.

Flower description:

*Flowering habit*.—Single and semi-double rotate flowers arranged in axillary compound cymes; freely flowering habit with about five flowers per cyme; flowers and face mostly outwardly to nodding.

*Fragrance*.—None detected.

*Natural flowering season*.—Plants begin flowering about eight weeks after planting; long flowering period, plants flower freely and continuously from spring until October in The Netherlands.

*Flower longevity*.—Individual flowers last about ten days on the plant; flowers not persistent.

*Inflorescence height*.—About 17.2 cm.

*Inflorescence diameter*.—About 8.7 cm.

*Flowers*.—Female flowers, diameter: About 4.5 cm. Female flowers, depth (height): About 2.9 cm. Male flowers, diameter: About 4.5 cm. Male flowers, depth (height): About 2.8 cm.

*Flower buds*.—Length, female flowers: About 1.9 cm. Diameter, female flowers: About 6 mm. Length, male flowers: About 1.4 cm. Diameter, male flowers: About 1.2 cm. Shape, female flowers: Ovate. Shape, male flowers: Broadly ovate, flattened. Color, female and male flowers: Close to 145B; towards the margins, tinged with close to 179C.

*Tepals*.—Quantity per flower: Female flowers, usually about five per flower; male flowers, usually about four per flower. Length, female flowers: About 2.9 cm. Width, female flowers: About 1.2 cm. Length, male flowers: About 3.3 cm to 3.4 cm. Width, male flowers: About 1.4 cm to 2.5 cm. Shape, female flowers: Narrowly ovate to narrowly obovate. Shape, male flowers: Narrowly elliptic or broadly elliptic. Apex, female and male flowers: Obtuse to praemorse. Margin, female and male flowers: Entire. Texture, female and male flowers, upper and lower surfaces: Smooth, glabrous; slightly velvety. Color, female flowers: When opening, upper surface: Close to 155A. When opening, lower surface: Close to 179D. Fully opened, upper surface: Close to N155C. Fully opened, lower surface: Close to 65D to lighter than 65D. Color, broadly elliptic male flowers: When opening, upper surface: Close to 158C; towards the margins, close to 48C to 48D. When opening, lower surface: Close to 39C to 39D. Fully opened, upper surface: Close to 158C; towards the margins, close to 48C to 48D. Fully opened, lower surface: Close to 55C to 55D; towards the margins, close to 54D; towards the base, close to 38C. Color, narrowly elliptic male flowers: When opening, upper surface: Close to 155A to 155B. When opening, lower surface: Close to 155A. Fully opened, upper surface: Close to N155C. Fully opened, lower surface: Close to 155A to 155B.

*Tepaloids*.—Quantity per flower: Present only on male flowers, usually about five per flower. Length: About 1.5 cm. Width: About 4 mm. Shape: Narrowly elliptic.

Apex: Obtuse to praemorse. Margin: Entire. Texture, upper and lower surfaces: Smooth, glabrous; slightly velvety. Color: When opening and fully opened, upper surface: Close to NN155A to NN155B; towards the base, close to 4C. When opening and fully opened, lower surface: Close to 4D; towards the base, close to 4C.

*Peduncles*.—Angle: About 30° from vertical. Strength: Moderately weak. Length: About 9.4 cm. Diameter: About 3 mm. Texture: Smooth, glabrous. Color: Close to 146B to 146C occasionally tinged with close to 175A.

*Pedicels*.—Angle: About 35° from the peduncle. Strength: Moderately weak. Length: About 3.2 cm. Diameter: About 1.5 mm. Texture: Smooth, glabrous. Color: Close to 174D; upper surface occasionally tinged with close to 179A.

*Reproductive organs*.—Female flowers: Number of pistils: About six per flower. Pistil length: About 8 mm. Style length: About 2 mm. Style color: Close to 9C. Stigma color: Close to 9A to 9B. Ovary color: Close to 144B. Male flowers: Number of stamens: About 40 per flower. Filament length: About 2.5 mm. Filament color: Close to 9B. Anther length: About 0.75 mm. Anther shape: Club-shaped. Anther color: Close to 13A to 13B. Pollen amount: Scarce. Pollen color: Close to 13B to 13C.

*Seed/fruit*.—Seed and fruit production have not been observed on plants of the new *Begonia*.

Disease/pest resistance: Resistance to pathogens and pests common to *Begonia* has not been observed on plants of the new *Begonia*.

Temperature tolerance: Plants of the new *Begonia* have been observed to tolerate temperatures from about 5° C. to about 35° C.

It is claimed:

1. A new and distinct *Begonia* plant named 'BKBEWPF' as illustrated and described.

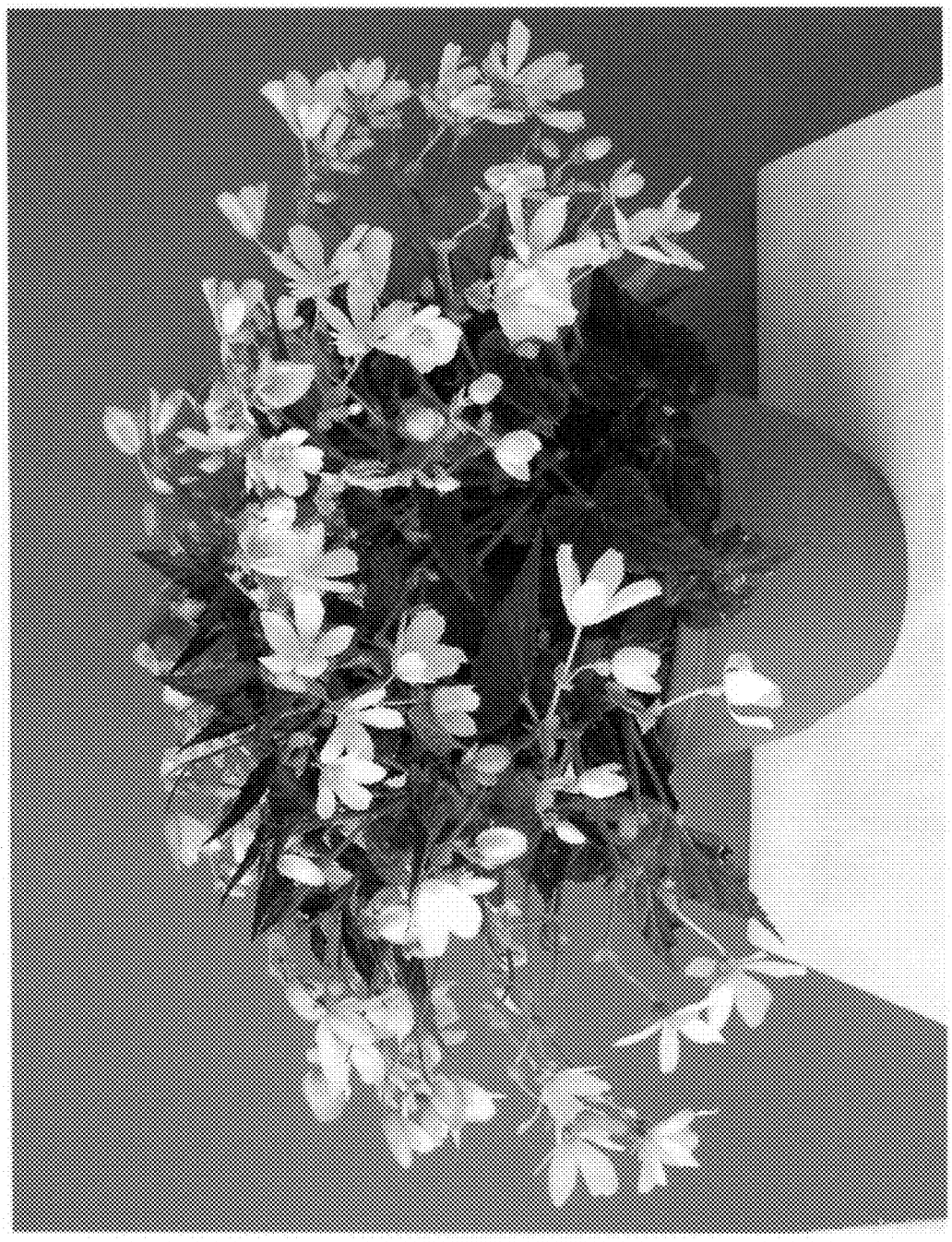

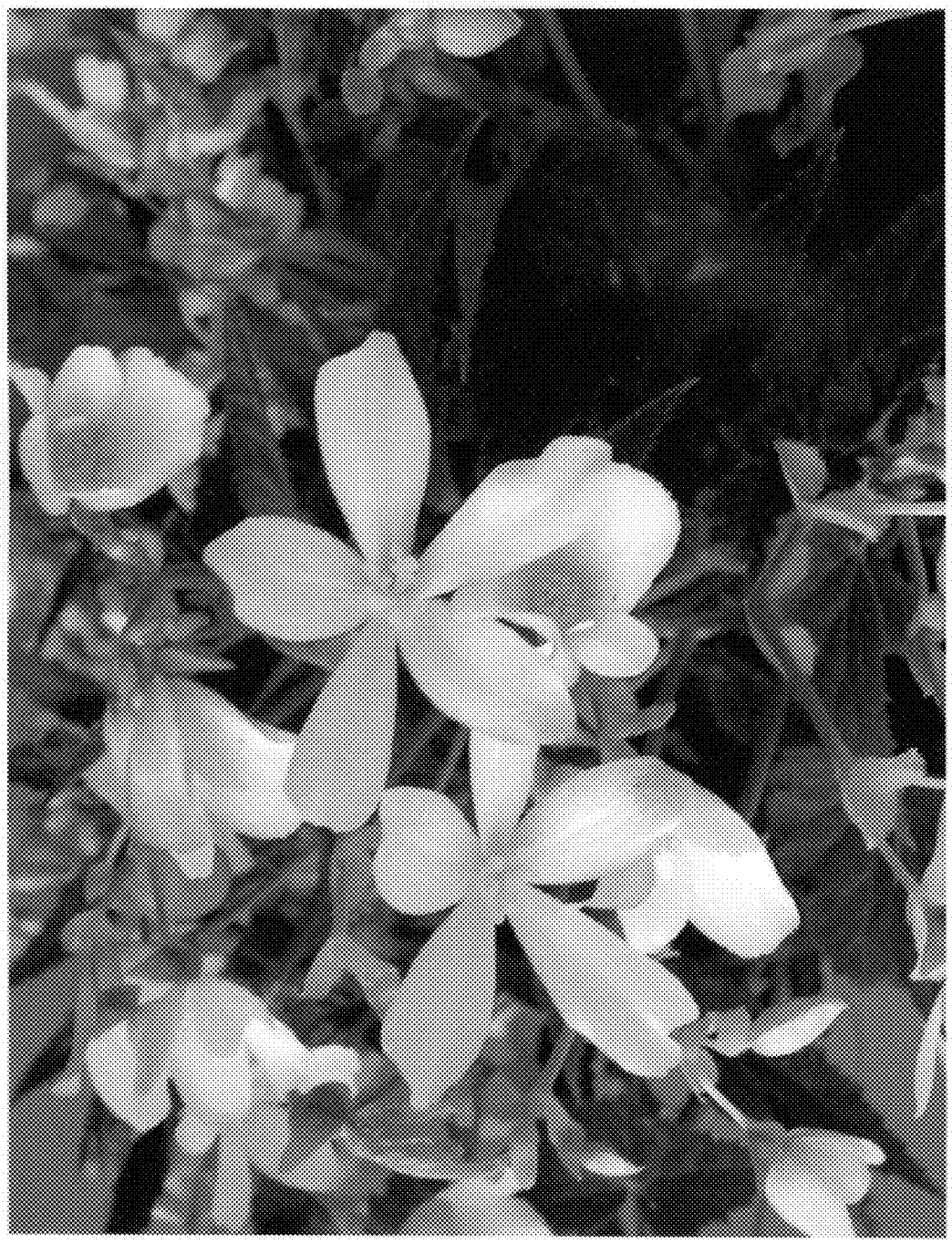

* * * * *